US008771166B2

(12) United States Patent
Conn et al.

(10) Patent No.: US 8,771,166 B2
(45) Date of Patent: Jul. 8, 2014

(54) IMPLANTABLE AUDITORY STIMULATION SYSTEM AND METHOD WITH OFFSET IMPLANTED MICROPHONES

(75) Inventors: Brian M. Conn, Broomfield, CO (US); José H. Bedoya, Boulder, CO (US)

(73) Assignee: Cochlear Limited, Macquarie University (AU)

( * ) Notice: Subject to any disclaimer, the term of this patent is extended or adjusted under 35 U.S.C. 154(b) by 749 days.

(21) Appl. No.: 12/790,404

(22) Filed: May 28, 2010

(65) Prior Publication Data
US 2010/0317913 A1    Dec. 16, 2010

Related U.S. Application Data (60) Provisional application No. 61/182,627, filed on May 29, 2009.

(51) Int. Cl.
*H04R 25/00*    (2006.01)

(52) U.S. Cl.
USPC .......................................................... 600/25

(58) Field of Classification Search
USPC ................. 600/25; 73/585; 181/126, 129; 381/23.1, 1, 92; 623/24; 607/55
See application file for complete search history.

(56) References Cited

U.S. PATENT DOCUMENTS

| | | | |
|---|---|---|---|
| 3,875,349 A * | 4/1975 | Ruegg | 381/313 |
| 4,443,666 A | 4/1984 | Cote | |
| 4,450,930 A | 5/1984 | Killion | |
| 4,504,703 A | 3/1985 | Schneiter et al. | |
| 4,532,930 A | 8/1985 | Crosby et al. | |
| 4,606,329 A | 8/1986 | Hough | |
| 4,607,383 A | 8/1986 | Ingalls | |
| 4,621,171 A | 11/1986 | Wada et al. | |
| 4,774,933 A | 10/1988 | Hough et al. | |
| 4,815,560 A | 3/1989 | Madaffari | |
| 4,837,833 A | 6/1989 | Madaffari | |

(Continued)

FOREIGN PATENT DOCUMENTS

| | | |
|---|---|---|
| WO | 0191678 | 12/2001 |
| WO | 2004024212 | 3/2004 |

(Continued)

OTHER PUBLICATIONS

Specification sheet for beyerdynamic MCE 60 Condenser Microphone, pp. 1-2, accessible online at http://north-america.beyerdynamic.com/shop/mce-60-09-cable-with-free-ends-4.html, available Feb. 21, 2009.*

(Continued)

*Primary Examiner* — Jacqueline Cheng
*Assistant Examiner* — Eileen Foley
(74) *Attorney, Agent, or Firm* — Lowe Hauptman & Ham, LLP (57) ABSTRACT

An improved implantable auditory stimulation system includes two or more implanted microphones for transcutaneous detection of acoustic signals. Each of the implanted microphones provides an output signal. The microphone output signals may be combinatively utilized by an implanted processor to generate a signal for driving an implanted auditory stimulation device. The implanted microphones may be located at offset subcutaneous locations and/or may be provided with different design sensitivities, wherein combinative processing of the microphone output signals may yield an improved drive signal. In one embodiment, the microphone signal may be processed for beamforming and/or directionality purposes.

26 Claims, 6 Drawing Sheets (56) References Cited

U.S. PATENT DOCUMENTS

| | | | |
|---|---|---|---|
| RE33,170 E | 2/1990 | Byers | |
| 4,932,405 A | 6/1990 | Peeters et al. | |
| 4,936,305 A | 6/1990 | Ashtiani et al. | |
| 5,015,224 A | 5/1991 | Maniglia | |
| 5,105,811 A | 4/1992 | Kuzma | |
| 5,163,957 A | 11/1992 | Sade et al. | |
| 5,176,620 A | 1/1993 | Gilman | |
| 5,276,739 A * | 1/1994 | Krokstad et al. | 381/318 |
| 5,277,694 A | 1/1994 | Leysieffer et al. | |
| 5,363,452 A | 11/1994 | Anderson | |
| 5,411,467 A | 5/1995 | Hortmann et al. | |
| 5,456,654 A | 10/1995 | Ball | |
| 5,554,096 A | 9/1996 | Ball | |
| 5,558,618 A | 9/1996 | Maniglia | |
| 5,624,376 A | 4/1997 | Ball et al. | |
| 5,702,431 A | 12/1997 | Wang et al. | |
| 6,039,685 A | 3/2000 | Bushek | |
| 6,325,755 B1 | 12/2001 | Bushek et al. | |
| 6,482,144 B1 | 11/2002 | Muller | |
| 6,517,476 B1 | 2/2003 | Bedoya et al. | |
| 6,554,761 B1 * | 4/2003 | Puria et al. | 600/25 |
| 6,648,914 B2 * | 11/2003 | Berrang et al. | 623/10 |
| 6,786,860 B2 | 9/2004 | Maltan et al. | |
| 6,807,445 B2 | 10/2004 | Baumann et al. | |
| 7,197,152 B2 | 3/2007 | Miller et al. | |
| 7,204,799 B2 | 4/2007 | Miller, III et al. | |
| 7,204,800 B2 | 4/2007 | Easter et al. | |
| 7,214,179 B2 * | 5/2007 | Miller et al. | 600/25 |
| 7,354,394 B2 | 4/2008 | Slattery, III et al. | |
| 7,489,793 B2 | 2/2009 | Miller, III et al. | |
| 7,522,738 B2 | 4/2009 | Miller, III | |
| 7,556,597 B2 | 7/2009 | Miller, III et al. | |
| 7,775,964 B2 | 8/2010 | Miller, III | |
| 7,822,479 B2 | 10/2010 | Stracener | |
| 7,840,020 B1 | 11/2010 | Miller, III et al. | |
| 2002/0032401 A1 | 3/2002 | Fereira et al. | |
| 2003/0031336 A1 | 2/2003 | Harrison et al. | |
| 2003/0055311 A1 * | 3/2003 | Neukermans et al. | 600/25 |
| 2005/0005421 A1 * | 1/2005 | Wang et al. | 29/594 |
| 2005/0101832 A1 | 5/2005 | Miller III et al. | |
| 2006/0183965 A1 * | 8/2006 | Kasic et al. | 600/25 |
| 2007/0016267 A1 | 1/2007 | Griffin et al. | |
| 2007/0167671 A1 * | 7/2007 | Miller III | 600/25 |
| 2007/0217640 A1 * | 9/2007 | Maltan et al. | 381/322 |
| 2007/0280495 A1 * | 12/2007 | Abolfathi | 381/326 |
| 2008/0049953 A1 * | 2/2008 | Harney et al. | 381/94.7 |
| 2008/0085023 A1 | 4/2008 | Kulkarni et al. | |
| 2008/0132750 A1 | 6/2008 | Miller | |
| 2008/0167516 A1 * | 7/2008 | Jaeger et al. | 600/25 |
| 2008/0234539 A1 * | 9/2008 | Slattery et al. | 600/25 |
| 2009/0163978 A1 | 6/2009 | Miller, III et al. | |
| 2009/0187065 A1 * | 7/2009 | Basinger | 600/25 |
| 2010/0272287 A1 | 10/2010 | Miller, III | |
| 2011/0034755 A1 | 2/2011 | Parker | |
| 2012/0109297 A1 | 5/2012 | Van den Heuvel | |

FOREIGN PATENT DOCUMENTS

| | | |
|---|---|---|
| WO | 2006081361 | 8/2006 |
| WO | 2009117767 | 10/2009 |
| WO | 2010126996 A1 | 11/2010 |

OTHER PUBLICATIONS

W. West, D. McMillan, "The Design of a Loud-Speaker," I.E.E. Wireless Proceedings, vol. 15, No. 44, Jun. 1940, pp. 1-67.*

C. Gibbons, R.N. Miles, "Design of a Biomimetic Directional Microphone Diaphragm," Proceedings of International Mechanical Engineering Congress and Exposition, Nov. 5-10, 2000, Orlando, FL, pp. 1-7.*

A.R. Leeuw, W.A. Dreshcler, "Advantages of Directional Hearing Aid Microphones Related to Room Acoustics," Audiology (1991) 30: 330-344.*

* cited by examiner

IMPLANTABLE AUDITORY STIMULATION SYSTEM AND METHOD WITH OFFSET IMPLANTED MICROPHONES

RELATED APPLICATIONS

This application claims priority to U.S. Provisional Application Ser. No. 61/182,627, filed May 29, 2009, entitled "IMPLANTABLE AUDITORY STIMULATION SYSTEM AND METHOD WITH OFFSET IMPLANTED MICROPHONES", the entirety of which is hereby incorporated by reference.

FIELD OF THE INVENTION

The present invention relates to implantable auditory stimulation systems, and more particularly, to an improved system and method that employs output signals from a plurality of implantable microphones to generate a stimulation drive signal.

BACKGROUND OF THE INVENTION

The utilization of implanted hearing instruments continues to increase. In this regard, implantable hearing devices provide operative and cosmetic advantages relative to conventional ear canal hearing devices. For example, implantable hearing devices offer operative advantages in relation to patient's having certain types of conductive or sensorineural hearing loss (e.g. mixed hearing loss comprising a conductive loss component of 45 dB or more with sensorineural hearing loss component of 40 dB or more). These patients are generally known to perform poorly with conventional hearing aids because their conductive and sensorineural hearing loss components are additive and these patients require substantial amounts of gain and output for proper speech recognition.

Typically, an implanted hearing instrument may comprise implanted componentry for stimulating a middle ear component of a patient's auditory system, or alternatively, for electrically stimulating a component of a patient's auditory system. In the former regard, one type of middle ear stimulation device includes an electromechanical transducer having a magnetic coil that drives a supported vibratory actuator positioned to contact and mechanically stimulate the ossicular chain of a patient. In another approach, a magnet is attached to the ossicular chain of a patient and a spaced coil is energized to generate a fluctuating magnetic field to induce magnet movement at acoustic frequencies.

In relation to electrical stimulation approaches, or auditory neurostimulation, known devices include auditory brain stem implant (ABI) devices and cochlear implant (CI) devices. In the case of CI devices an electrode array is inserted into the cochlea of a patient, e.g. typically into the scala tympani so as to access and follow the spiral currature of the cochlea. The array electrodes are selectively driven to stimulate the patient's auditory nerve endings to generate sound sensation. In this regard, a CI electrode array works by utilizing the tonotopic organization, or frequency-to-location mapping, of the basilar membrane of the inner ear. In a normal ear, sound vibrations in the air are transduced to physical vibrations of the basilar membrane inside the cochlea. High frequency sounds do not travel very far along the membrane, while lower frequency sounds pass further along. The movement of hair cells, located along the basilar membrane, creates an electrical disturbance, or potential, that can be picked up by auditory nerve endings that generate electrical action pulses that travel along the auditory nerve to the brainstem. In turn, the brain is able to interpret the nerve activity to determine which area of the basilar membrane is resonating, and therefore what sound frequency is being sensed. By directing which electrodes of a CI electrode array are activated, cochlear implants can selectively stimulate different parts of the cochlea and thereby convey different acoustic frequencies corresponding with a given audio input signal.

With ABI systems a plurality of electrodes may be implanted at a location that bypasses the cochlea. More particularly, an array of electrodes may be implanted at the cochlea nucleus, or auditory cortex, at the base of the brain to directly stimulate the brainstem of a patient. Again, the electrode array may be driven in relation to the tonotopic organization of a recipient's auditory cortex to obtain the desired sound sensation.

As may be appreciated, in the case of either middle ear stimulation devices or neurostimulation devices, audio signals from a microphone may be processed, typically utilizing what is referred to as a speech processor, to generate signals to drive the stimulation device. In this regard, as implanted hearing instruments have continued to evolve, the utilization of implanted microphones has increased. However, the employment of implanted microphones has presented a number of challenges in relation to realizing a desired signal-to-noise ratio with adequate sensitivity across a normal hearing range of acoustic frequencies.

SUMMARY OF THE INVENTION

The present invention is directed to an improved implantable auditory stimulation system and method that contemplates the utilization of a plurality of implanted microphones to provide a corresponding plurality of output signals which may be combinatively employed in the generation of a signal to drive an implantable auditory stimulation device. In this regard, the present inventors have recognized the advantage of utilizing multiple microphones that may be located at differing subcutaneous locations having differing acoustic and vibrational characteristics. The present inventors have also recognized the benefit of utilizing a plurality of microphones that may be located at offset subcutaneous locations to facilitate the utilization of the multiple microphone output signals for beamforming and directionality purposes. Additionally, the present inventors have recognized the advantage of employing multiple implanted microphones having different design sensitivities.

An improved implantable auditory stimulation system may comprise a plurality of implantable microphones, including at least a first microphone operative to transcutaneously receive acoustic signals and generate a first microphone output signal in response thereto, and a second microphone operative to transcutaneously receive acoustic output signals and generate a second microphone output signal in response thereto. The system may further include a processor (e.g. a speech processor), operatively interconnected to the first microphone and to the second microphone, adapted to combinatively use the first and second microphone output signals to generate a drive signal. In turn, the system may employ an implantable auditory stimulation device, operatively interconnected to the processor, to stimulate an auditory system component of a patient in response to the drive signal.

In one aspect, at least a first microphone may be disposed within an implantable first housing and at least a second microphone may be disposed within an implantable second housing, wherein the first and second housings are structurally separate, e.g., not fixedly interconnected. In this regard, the first and second implantable housings may be separately positioned at spaced subcutaneous locations. By way of example, in one arrangement the first housing may be disposed on a patient's skull (e.g. on the temporal bone posterior to the external auditory canal), while the second microphone may be disposed on soft tissue of the patient (e.g. near the sterno-cleido-mastoid muscle). In the later regard, soft tissue placement may be provided as taught by U.S. Pat. No. 7,354,394, hereby incorporated by reference in its entirety.

In another aspect, a first microphone may be disposed within an implantable housing and a second microphone may be disposed within the same implantable housing but separated in distance across the housing. In this device, the position of the first and second microphones within the housing may be chosen for optimal placement relative to a patient's physiological features in relation to contemplated processing of the microphone output signals. For example, the position of the first microphone may be chosen for optimal placement near the external auditory canal, whereas the position of the second microphone may be chosen for optimal placement near the temporalis muscle. The microphone output signals may then be combinatively employed.

It should be appreciated that numerous combinations of two or more implantable microphones can be envisioned in which the microphones are grouped in either the same or separate housings to achieve specific acoustic amplification and signal processing purposes. In this regard, it should also be appreciated that various combinations of implantable microphones may be employed in which more than two microphones are employed in the same or multiple housings.

In a further aspect, a plurality of implantable microphones may be disposed at offset implant locations, wherein a corresponding plurality of microphone output signals may be combinatively employed by a processing module of processor for beamforming and/or directionality purposes. In this regard, the plurality of microphones may be located in the same or separate implant housings.

In another aspect, at least a first microphone may be provided to have a first predetermined minimum sensitivity across a first predetermined frequency range, and at least a second microphone may be provided to have a second predetermined minimum sensitivity across a second frequency range, wherein the first and second predetermined frequency ranges are at least partially non-overlapping. In this regard, the sensitivities of the first and second microphones may be advantageously provided in corresponding relation to the acoustic and vibrational characteristic of the intended implant locations. Further, one or more additional microphones may be provided having corresponding predetermined minimum sensitivities across corresponding predetermined frequency ranges that may the same or at least partially non-overlapping with the first and second predetermined frequency ranges.

In one implementation, a first microphone may be provided for positioning on a patient's skull (e.g. posterior to the external auditory canal) with an implanted design sensitivity of at least approximately −60 to −50 dB V/0.1 Pa across a frequency range of about 50 $H_z$ to 3000 $H_z$. In the same or another implementation a second microphone may be provided for positioning on soft tissue of a patient (e.g. near the sterno-cleido-mastoid muscle) with an implanted design sensitivity of at least about approximately −60 to −50 dB V/0.1 Pa across a frequency range of about 1500 $H_z$ to 10000 Hz. Various filtering techniques can be employed to achieve roll-off above and below the band of interest.

In a further aspect, at least one of a first implantable microphone and a second implantable microphone may be operatively interconnected to the processor via at least a flexible first communication cable, thereby facilitating selective placement of the microphones at offset subcutaneous locations. In one approach, the first communication cable may have a first end that is one of fixedly interconnected to, and selectively interconnectable to and disconnectable from the processor.

In another approach, the first communication cable may have a first end that is one of fixedly interconnected to, and selectively interconnectable to and disconnectable from, an implantable connector, and a second end that is one of fixedly interconnected to, and selectively interconnectable to and disconnectable from one of the first microphone and second microphone. In turn, a flexible second communication cable may be utilized to operatively interconnect the connector to the processor. In this regard, the second communication cable may have a first end that is one of fixedly interconnected to, and selectively interconnectable to and disconnectable from, the processor, and a second end that is one of fixedly interconnected to, and selectively interconnectable to and disconnectable from, the implantable connector.

In the later regard, a flexible third communication cable may be provided having a first end that is one of fixedly interconnected to, and selectively interconnectable to and disconnectable from the auditory stimulation device, and a second end that is one of fixedly interconnected to, and selectively interconnectable to and disconnectable from the implantable connector. In another approach, the second end of the third communication cable may be one of fixedly interconnected to, and selectively interconnectable to and disconnectable from the processor.

The inclusion of one or more flexible communication cable(s) having one or both ends be adapted for selective interconnection to and disconnection from other system componentry facilitates replacement, servicing, and upgrading of system componentry, as well as migration of a patient from one type of auditory stimulation device to another (e.g. migration from a middle ear stimulation device to a cochlear stimulation device).

One cable end connector design that may be utilized is described in U.S. Pat. No. 6,517,476, hereby incorporated by reference in its entirety. Another cable end connector design and implantable connector that may be utilized is described in U.S. patent application Ser. No. 12/016,765, hereby incorporated by reference in its entirety.

In one approach, a processor may be located within an implantable first housing together with a first microphone. The processor may comprise analog and/or digital logic componentry for conditioning first and second microphone output signals separately and/or as combined. For example, analog filters may be employed to attenuate or shape the frequency response of the microphones. Analog circuits may also be applied to cancel signals. Digital signal processing via FIR or IIR filters may be applied for similar purposes. Additionally, frequency domain processing via FFT may be applied for frequency shaping or noise cancellation. In certain embodiments, signal noise cancellation may be facilitated via the inclusion of one or more motion sensor(s) (e.g. accelerometer(s)) disposed in one or more implantable housing(s) together with one or more microphones. In this regard, signal processing functionality may be included as taught by U.S. Patent Application Publication Nos. 2007/0167671, 2005/0101831, 2006/0155346, 2008/0132750 and U.S. Pat. No. 7,214,179, each of which is hereby incorporated by reference in its entirety. As noted above, the processor may also include a processing module beamforming and/or directionality purposes.

Additionally, in certain embodiments a power storage device (e.g. a rechargeable battery) and other componentry may be disposed within the first housing. Further, a receiver adapted to receive transcutaneous wireless signals may be interconnected to the first housing. In one approach, a receiver (e.g. an inductive coil) may be encapsulated by a biocompatible capsule that is interconnected to the first housing. Additional system componentry may be implemented, e.g. as disclosed in U.S. Patent Application Publication No. 2006/0183965, hereby incorporated by reference in its entirety.

An improved method for use with an implantable auditory stimulation system device is also provided. The method includes the step of positioning at least a first microphone at a first subcutaneous location, wherein the first microphone is operative to transcutaneously receive acoustic signals and generate a first microphone output signal in response thereto. The method additionally includes the step of locating at least a second microphone at a second subcutaneous location of the patient, wherein the second microphone is operative to transcutaneously receive acoustic signals and generate a second microphone output signal in response thereto. The method further provides for operatively interconnecting a processor to the first microphone and to the second microphone, wherein the processor is operative to combinatively use the first microphone output signal and the second microphone output signal to generate a drive signal to drive the implantable auditory stimulation device.

In one approach, at least a first microphone may be fixedly disposed within a first housing and at least a second microphone may be fixedly disposed within a separate second housing, wherein the first and second housings may be separately positioned at offset subcutaneous locations. In another approach, at least two microphones may be disposed at offset locations within a common housing.

In another aspect, two or more microphones may be offset with at least a predetermined spacing therebetween to facilitate combinative use of the microphone output signals by a processor for beamforming or directionality purposes. That is, offset microphones may be disposed and their output signals processed to simulate natural hearing, e.g. so that acoustic signals received by a patient from a forward direction are perceived more prominently than acoustic signals received by a patient from a rearward direction.

In one aspect, the positioning of a first microphone may entail locating a corresponding first housing in spaced relation to a surface of a skull of the patient, wherein the first microphone is at least partially isolated from skull borne vibrations by soft tissue disposed between the first microphone and the skull of a patient. In a related aspect, positioning of a second microphone may provide for mounting a corresponding second housing to the skull of a patient.

In yet another aspect, the method may further includes the steps of sensing acoustic signals at a first microphone with a first predetermined minimum sensitivity across a first frequency range, and sensing acoustic signals at a second microphone with a second predetermined minimum sensitivity across a second frequency range, wherein the first and second microphone output signals are provided. The first and second frequency ranges may be at least partially overlapping.

In the various embodiments, the processor may combinatively process the multiple microphone signals and generate an appropriate drive signal. In turn, an auditory stimulation device may utilize the drive signal to stimulate a component of a patient's auditory system.

Additional features and advantages will become apparent to those skilled in the art upon consideration of the further description that follows.

DETAILED DESCRIPTION

Figure 1:
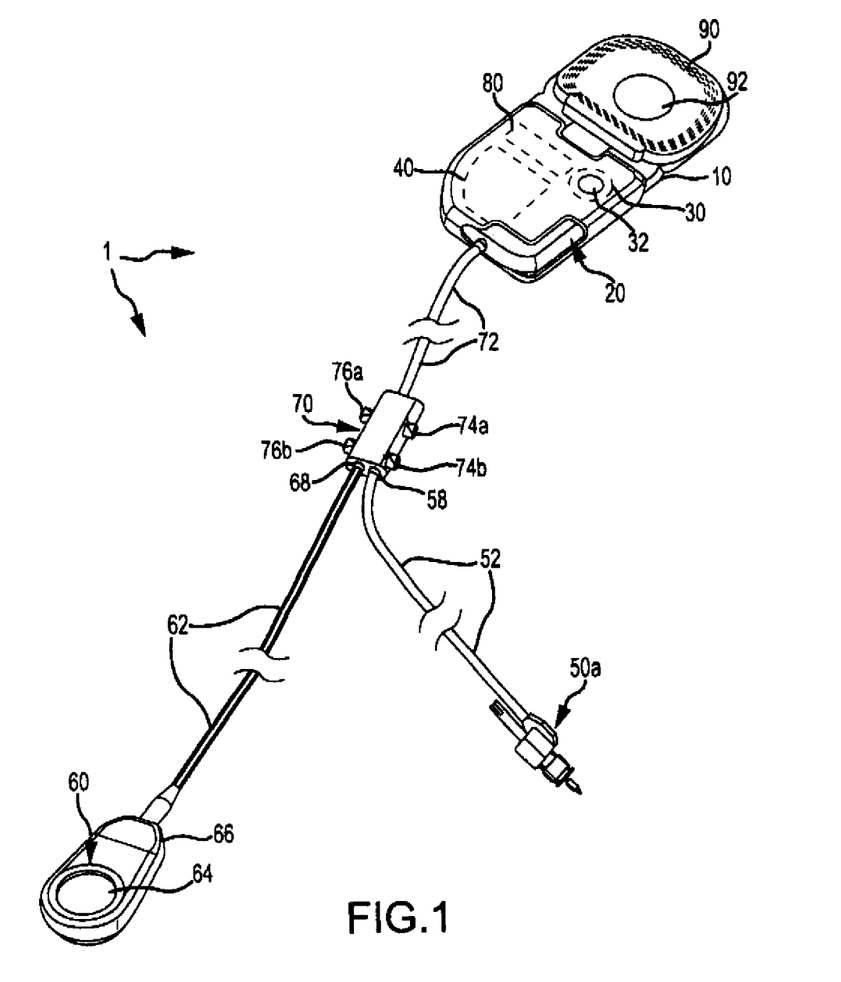
FIG. 1 illustrates an embodiment of an implantable auditory stimulation system for middle ear stimulation.
Figure 2:
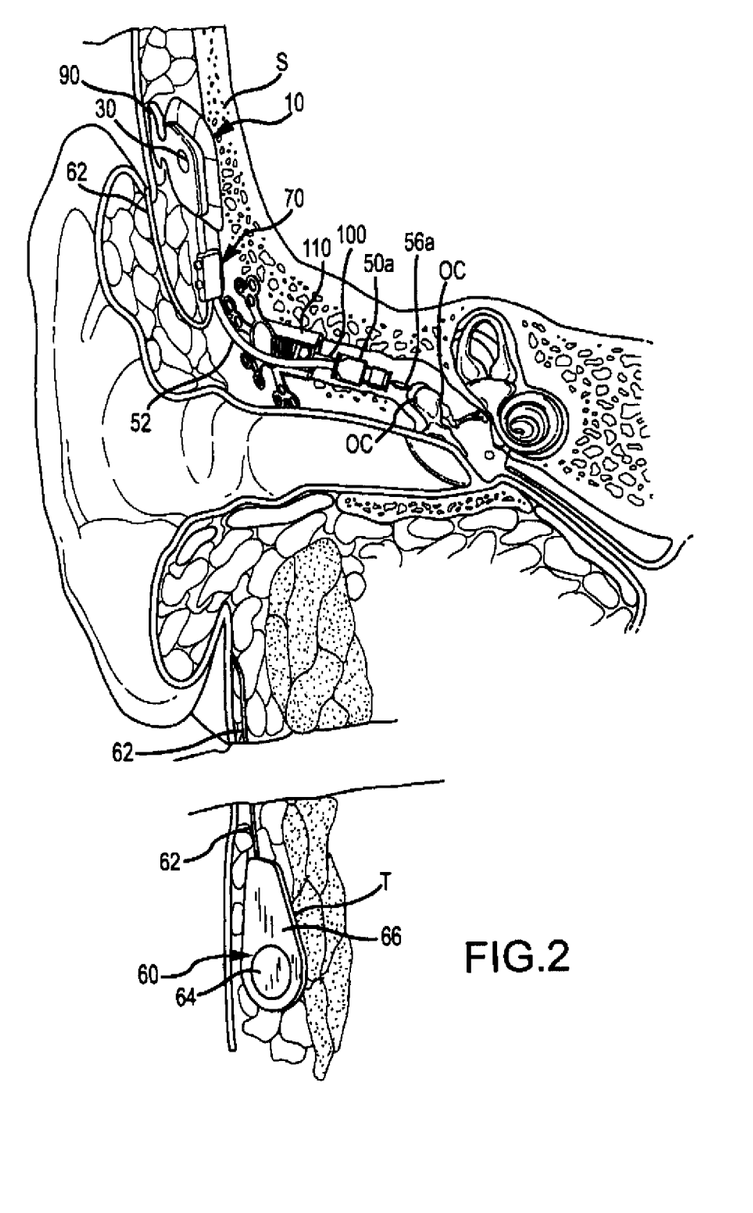
FIG. 2 illustrates the embodiment of FIG. 1 in an implanted arrangement.

FIGS. 1 and 2 illustrate one embodiment of an implantable auditory stimulation system 1. The system 1 may include a first housing 20 that houses a first microphone 30 for transcutaneous receipt of acoustic signals. In one approach, the first microphone 30 may include a diaphragm 32 disposed at a skin-facing side of the first housing 20. The first housing 20 may further house a processor 40 for processing an audio output signal from the first microphone 30, as well as additional componentry noted hereinbelow.

The system 1 may also include a second microphone 60 located in a second housing 66. In one approach, the first microphone 60 may include a diaphragm 64 disposed at a skin-facing side of the second housing 66. The second microphone 60 may be operatively interconnected with the processor 40, wherein the processor 40 may process an audio output signal from the second microphone 60. In this regard, the processor 40 may utilize audio output signals from both the first microphone 30 and second microphone 60 to generate a drive signal.

In turn, the system may include an auditory stimulation device 50a for stimulating a patient's auditory system in response to the drive signal. In the illustrated embodiment, the auditory stimulation device 50a is for middle ear stimulation, e.g. an electromechanical transducer.

Electrical interconnections between the second microphone 60 and auditory stimulation device 50 and signal processor 40 may be realized via the inclusion of a connector 70 that may be electrically interconnected with signal processor 40 via a flexible communication cable 72. As shown, the communication cable 72 may be fixedly interconnected at one end to the implantable housing 20 and processor 40 housed therein, and to the connector 70 at the other end. Alternatively, one or both ends of the communications cable 72 may be provided to be selectively interconnectable to and disconnectable the implantable housing 20 and/or connector 70.

As shown in FIG. 1, the second microphone 60 and auditory stimulation device 50 may be electrically interconnected to connector 70 via corresponding flexible communication cables 62 and 52, respectively. The communication cables 62 and 52 may be fixedly interconnected or selectively interconnectable/disconnectable to connector 70 at first connector ends 68 and 58, respectively. In this regard, and as shown in FIG. 1, connector 70 may be provided with advanceable/retractable locking members 74a, 74b for selective, secure interconnection of connector 70 to a connector end 58 of communication cable 52 that may be inserted into an interface aperture of connector 70. Further, connection 70 may be provided with locking members 76a, 76b for selective secure interconnection of connection 70 to a connector end 68 of communication cable 62 that may be inserted into an interface aperture connection 70.

Additionally, a second end of communication cable 52 may be fixedly interconnected to auditory stimulative device 50, as shown in FIG. 1, or selectively interconnectable to and disconnectable from auditory stimulation device 50. Similarly, a second end of communication cable 62 may be fixedly interconnected to second microphone 60, as shown, or selectively interconnectable to and disconnectable from second microphone 60.

The optional interconnectability/disconnectability features noted above may be employed to facilitate the ability to service, upgrade, and/or replace componentry, or to migrate from one type of auditory stimulation device 50 to another, without removal of other implant system componentry. In turn, medical personnel efficiencies and enhanced patient care may be realized.

In some implementations, an implantable capsule 10 may be provided that carries an antenna 90 (e.g. an inductive coil) adapted to receive and/or transmit transcutaneous wireless signals from an external antenna, as well as a magnet 92 that functions with an external magnet to maintain positioning of an external wireless signal transmitter and/or receiver. In this regard, the capsule 10 may encapsulate the antenna 90, magnet 92, housing 20 and electrical interconnections between antenna 90 and housing 20. For purposes of illustration, a portion of capsule 10 is cut-away in FIG. 1 to show the housing 20. The inclusion of capsule 10 facilitates interconnected positioning of housing 20 and antenna 90 during implant procedures. In one approach, capsule 10 may comprise an over-molded, silicon-based material.

By way of example, the antenna 90 may be provided to receive transcutaneous signals that comprise radio frequency (RF) power signals. In turn, the RF power signals may be utilized for powering the various implanted componentry. In one approach, the housing 20 may further include a power storage device 80 (e.g. a rechargeable battery), wherein the RF power signals are received and converted to an electrical signal by antenna 90, and then utilized to recharge the power storage device 80.

In certain arrangements, the transcutaneous signals may comprise RF audio signals. By way of example, such RF audio signals may comprise audio signals generated by external devices such as audio equipment, telephones (e.g. cellular telephones), assistive listening devices, external microphones and/or external headsets (e.g. Bluetooth headsets). In turn, the RF audio signals may be utilized by processor 40 to provide a drive signal to the auditory stimulation device 50a.

Reference is now made to FIG. 2 which illustrates the system 1 of FIG. 1 in an implanted state. As shown, the housing 20 may be located at a first location on the skull of a patient. Such skull placement provides for stable positioning of the first microphone 20, thereby yielding a stable transfer function between acoustic signals received at the first microphone 30 and the audio output signal generated in response thereto. Further, placement of first microphone 30 at the skull interface location illustrated in FIG. 2 offers the advantage of a relatively constant and thin skin thickness overlying the diaphragm of the first microphone 30, thereby enhancing the transfer function, as well as reducing the low frequency content of the microphone output signal due to body noise as compared to microphones placed in soft tissue. Microphones placed in soft tissue are typically subject to large amplitude low frequency signals due to both the patient's own voice as well as due to gross movements of the muscles of the neck.

The positioning of the second microphone 60 on soft tissue of a patient, e.g. in the neck region illustrated in FIG. 2, yields the advantage of isolating the second microphone 60 from skull-borne vibrations. In this regard, skull-borne vibrations may result from operation of an auditory stimulation device 50a. Skull-borne vibration may also arise naturally from a patient's own voice, chewing or coughing. In each of the noted cases, vibrations may be transmitted to the site of an implanted microphone, received by a microphone diaphragm, and then amplified, thereby introducing undesired noise into the system. Positioning of second microphone 60 on soft tissue of a patient reduces such noise in the audio output signal of second microphone 60.

As shown in FIG. 2 the auditory stimulation device 50a may be supportably connected to a positioning system 100, which in turn, may be connected to a bone anchor 110 mounted within a patient's mastoid process (e.g. via a hole drilled into the cortical surface of the skull). In the illustrated embodiment, auditory stimulation device 50a may comprise an actuator 56a for contact interface with the ossicular chain OC of the patient. As shown, the actuator 56a may provide for mechanical stimulation of the ossicular chain, e.g. through the transmission of vibrations to the incus of the patient's ossicular chain.

The processor 60 may comprise circuitry and other analog componentry and/or digital componentry for processing the audio output signals from the first microphone 30 and from the second implanted microphone 60. Such componentry may provide for frequency shaping, amplification, weighting, compression and other signal conditioning steps, including conditioning based on patient-specific fitting parameters. One or more of such conditioning steps may be provided separately in relation to the audio output signals from the first microphone 30 and from the second microphone 60. Additionally and/or alternatively, one or more such signals conditioning steps may be carried out during or after processor 60 has combined the audio output signals from first microphone 30 and second microphone 60. For example, circuits and/or signal processing algorithms may cancel electrical noise, unwanted signals such as body generated noise or the patient's own voice, or signal processing artifacts. Additionally, algorithms for beamforming or directionality may be employed.

In relation to the first microphone 30 and second microphone 60, such microphones may be advantageously designed to yield different sensitivity characteristics in relation to the corresponding intended placement of such microphones. By way of example, in one embodiment the first microphone 30 may be provided to have a sensitivity of at least approximately −60 to −50 dB V/0.1 Pa across a frequency range of about 50 $H_z$ to 3000 Hz. Second microphone 60 may be designed to have a minimum sensitivity of approximately −60 to −50 dB V/0.1 Pa across a frequency over an acoustic frequency range of between about 1500 $H_z$ to 10000 $H_z$. By virtue of such offset sensitivity characteristics the output signals from the first microphone 30 and second microphone 60 may be combinatively processed to yield an enhanced drive signal for driving the auditory stimulation device 50a.

Figure 3:
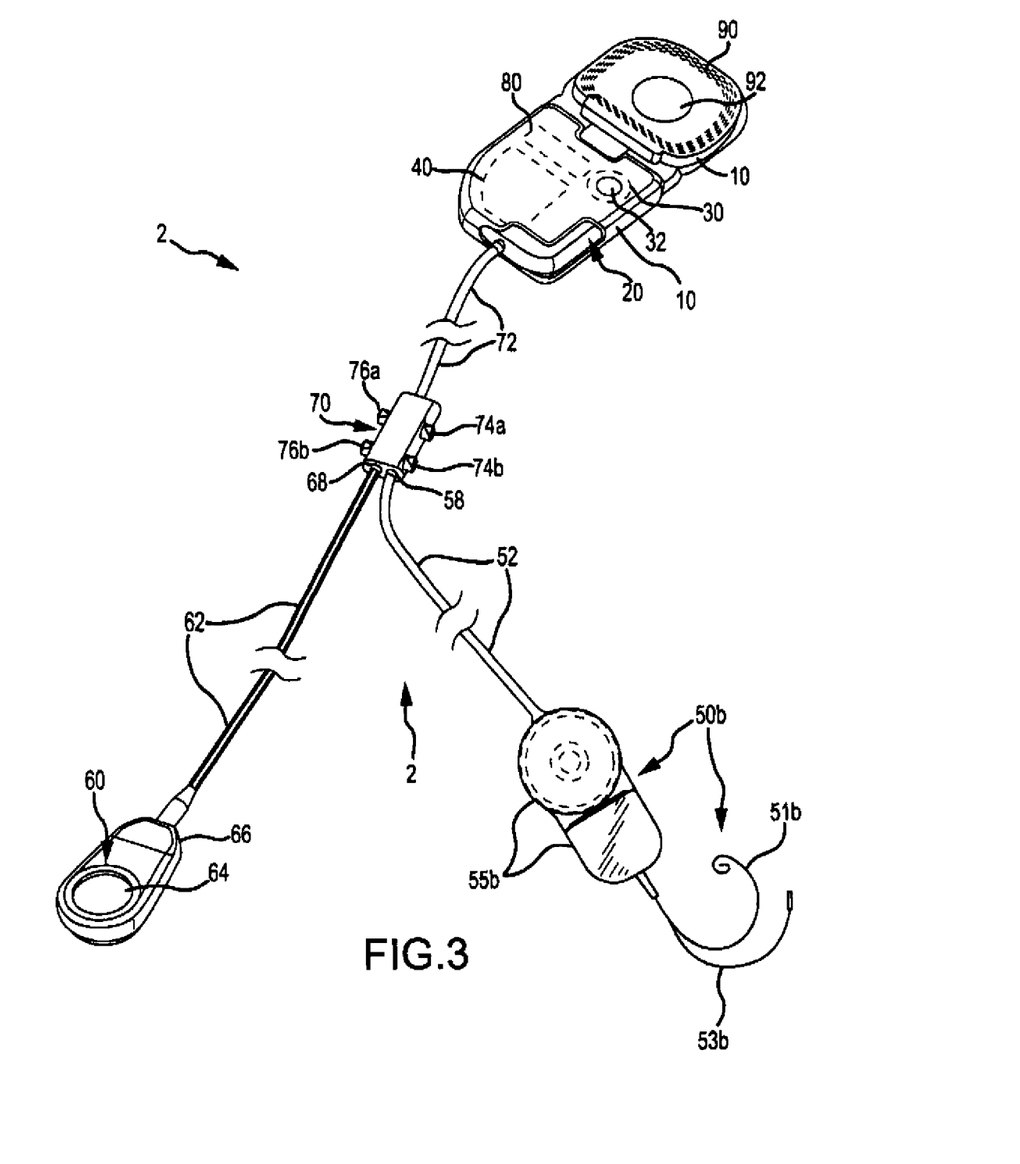
FIG. 3 illustrates an embodiment of an implantable auditory stimulation system for cochlear stimulation.
Figure 4:
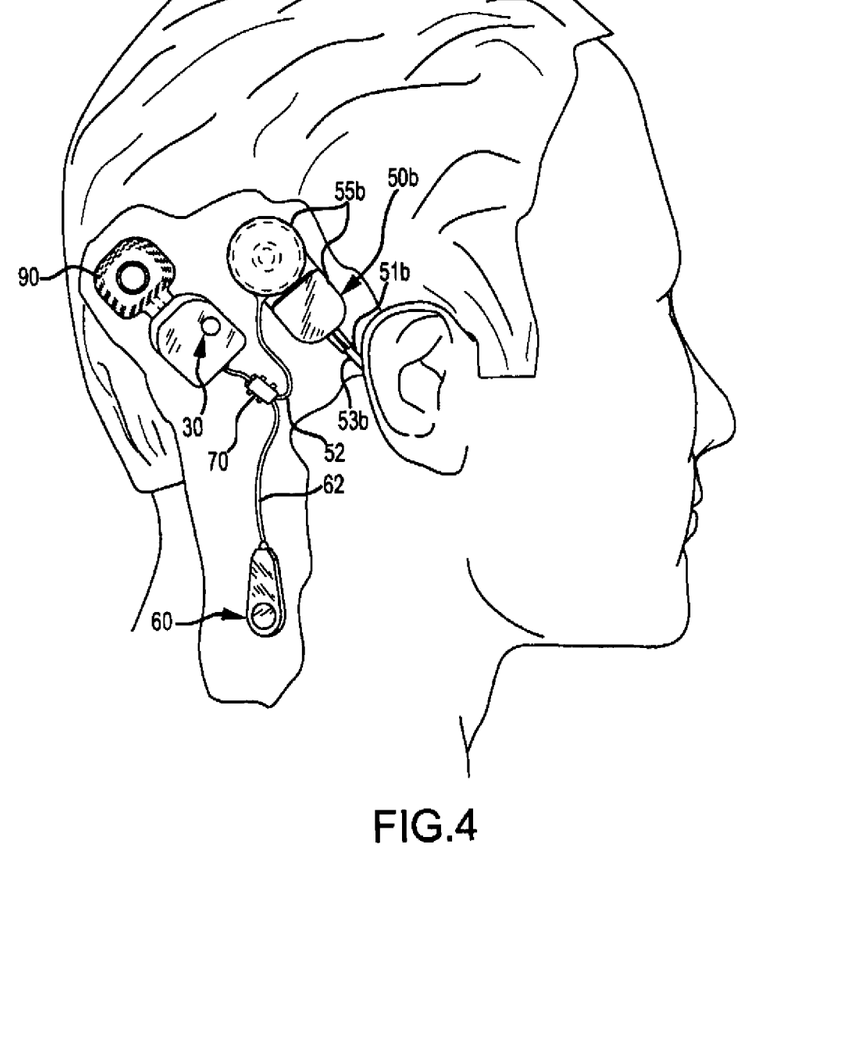
FIG. 4 illustrates the embodiment of FIG. 3 in an implanted arrangement.

Reference is now made to FIGS. 3 and 4 which illustrates one embodiment of an implantable auditory stimulation system 2 that includes an auditory stimulation device 50b in the form of a cochlear implant stimulation device. In this regard, the cochlear implant stimulation device 50b shown in FIG. 3 may include an electrode array 51a for insertion into a patient's cochlea, a reference electrode 53a (e.g. for interconnection to a patient's skull typically near the temporalis muscle), and an optional module 55a for wireless interface with external componentry and/or for signal processing additional to that completed by processor 40. In the later regard, wireless input may be supplied to module 55b from external audio sources such as personal audio devices, microphones, or external speech processors. Other components of the system 2 may be the same as described above in relation to system one of FIGS. 1 and 2.

Figures 5, 6:
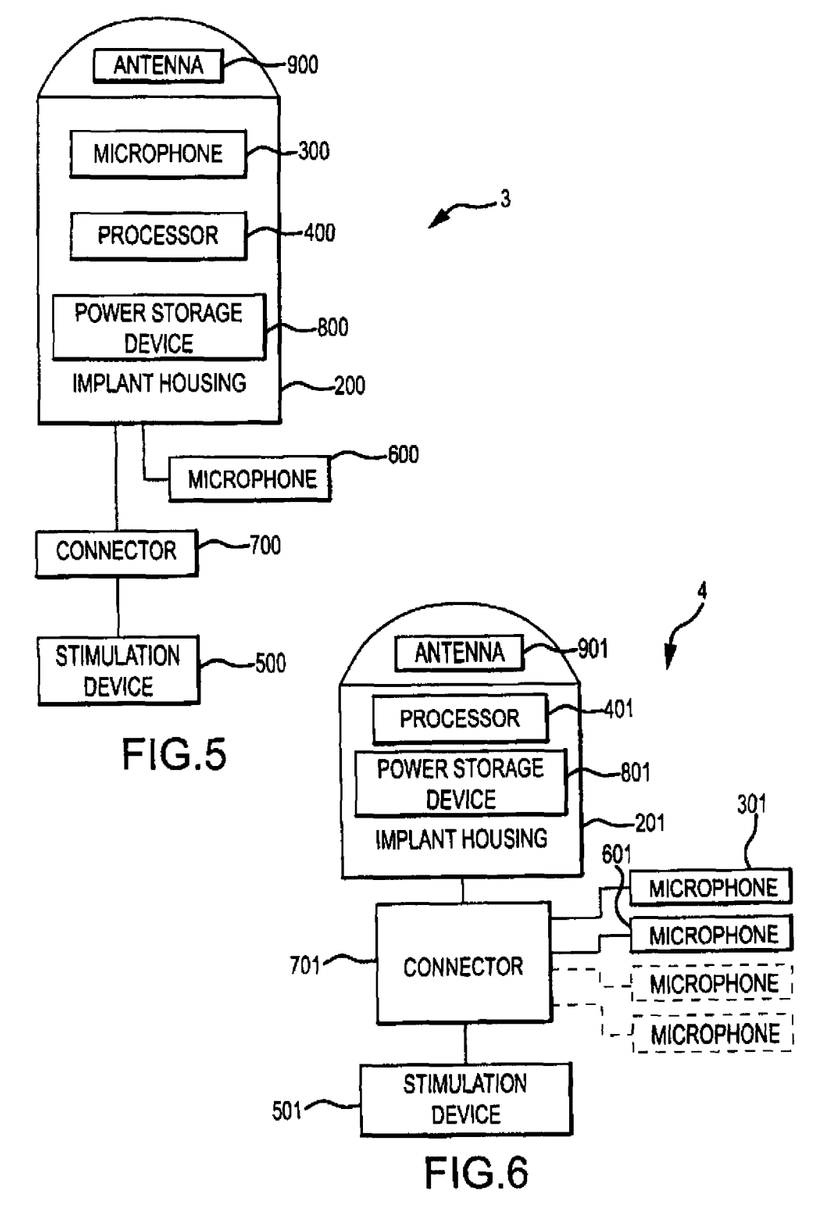
FIGS. 5, 6, 7 and 8 schematically illustrate additional embodiments of implantable auditory stimulation systems.

Reference is now made to FIGS. 5-8 which schematically illustrate additional embodiments of implantable auditory stimulation systems. In FIG. 5 an implantable auditory stimulation system 3 includes an implant housing 200 that may house at least a first microphone 300, a processor 400 and other componentry (e.g. power storage device 800). The implant housing 200 may be structurally interconnected to a antenna 900 (e.g. an indicative coil) for receiving and/or transmitting wireless transcutaneous signals.

At least a second implantable microphone 600 (e.g. located in a separate implant housing) may be operatively interconnected or interconnectable to the processor 403 at implant housing 200. Output signals from the first microphone 300 and the second microphone 600 may be combinatively processed by the processor 400 to generate a drive signal.

In this regard, a stimulation device 500 may be interconnected or interconnectable to a connector 700 which may be interconnected or interconnectable to the processor 400 at implant housing 200. In turn, the drive signal generated by the processor 400 may be provided to the stimulation device 500. The stimulation device 500 may comprise a middle ear stimulation device and/or a neurostimulation device (e.g. a CI stimulation device or an ABI stimulation device).

FIG. 6 illustrates an implantable auditory stimulation system 4 that includes an implant housing 201 that may house a processor 401 and other componentry (e.g. a power storage device 801). The implant housing 201 may be structurally interconnected to an antenna 901 for receiving and/or transmitting wireless transcutaneous signals.

At least a first implantable microphone 301 and second implantable microphone 601 may be interconnected or interconnectable to the processor 401 at implant housing 201 via a connector 701 that may be interconnected or interconnectable to the processor 401 at implant housing 201. In turn, output signals from the first microphone 301 and the second microphone 601 may be combinatively processed by the processor 401 to generate a drive signal. As illustrated, additional microphones may be optionally interconnected via connector 701 to the processor 401 at implant housing 201, wherein output signals from such additional microphones may be combinatively employed with the output signals of the first implantable microphone 301 and second implantable microphone 601.

A stimulation device 501 may be interconnected or interconnectable via the connector 701 to the processor 401 at implant housing 201. In turn, the drive signal generated by the processor 401 may be provided to the stimulation device 501. The stimulation device 501 may comprise a middle ear stimulation device and/or neurostimulation device (e.g. a CI stimulation device or an ABI stimulation device).

Figures 7, 8:
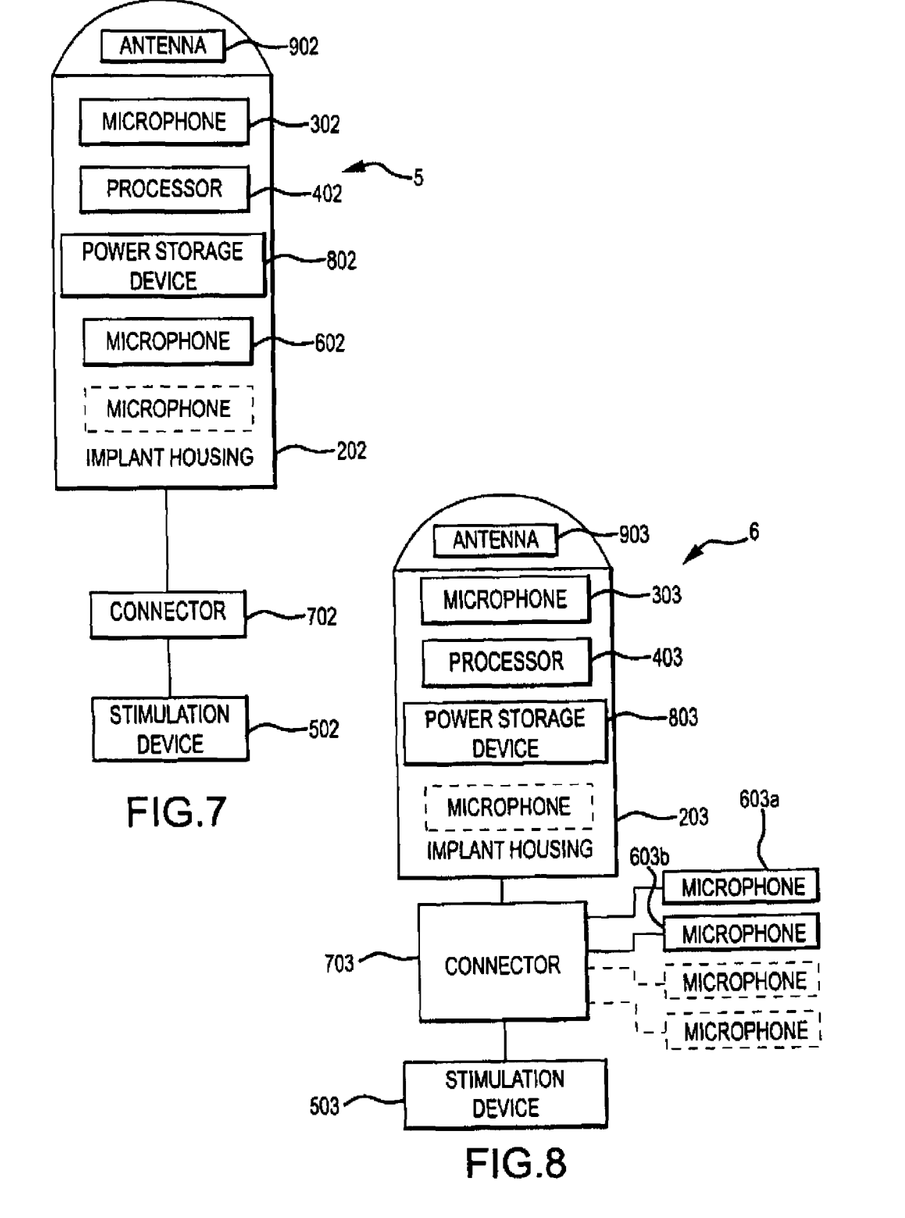

FIG. 7 illustrates a further implantable auditory stimulation system 5 that includes an implant housing 202 that may house a processor 402 and other componentry (e.g. a power storage device 802). Additionally, the implant housing 202 may house at least a first microphone 302 and a second microphone 602 at spatially offset locations. The output signals from the first microphone 302 and second microphone 602 may be combinatively processed by the processor 402 to generate a drive signal. As shown, additional microphones may also be disposed within implant housing 202.

In the illustrated arrangement, the implant housing 202 may be structurally interconnected to an antenna 902 for receiving and/or transmitting wireless transcutaneous signals. Such structural interconnection may be provided via an over-molded capsule (e.g. comprising a silicon-based material).

A stimulation device 502 may be interconnected or interconnectable via a connector 702 to the processor 402 at implant housing 202. In turn, the drive signal generated by the processor 402 may be provided to the stimulation device 502. The stimulation device 502 may comprise a middle ear neurostimulation device (e.g. a CI stimulation device or an ABI stimulation device).

FIG. 8 illustrates yet another implantable auditory stimulation system 6. The implantable auditory stimulation system 6 may include an implant housing 203 that houses at least a first microphone 303, a processor 403 and other componentry (e.g. a power storage device 803). The implant housing 203 may be structurally interconnected to an antenna 903 (e.g. an inductive coil) for receiving and/or transmitting wireless transcutaneous signals.

At least a second implantable microphone 603a (e.g. located in a separate implant housing) and a third implantable microphone 603b (e.g. located in a separate implant housing) may be operatively interconnected or interconnectable via a connector 703 to the processor 403 at implant housing 230. Output signals from the first microphone 303, second microphone 603a and third microphone 603b may be combinatively processed by the processor 403 to generate a drive signal.

In this regard, a stimulation device 503 may be interconnected or interconnectable to the connector 703. In turn, the drive signal generated by a processor 403 may be provided to the stimulation device 503. The stimulation device may comprise a middle ear stimulation device and/or neurostimulation device (e.g. a CI stimulation device or an ABI stimulation device).

Additional embodiments, implementations and additions to those described above will be apparent to those skilled in the art and are intended to be within the scope of the present invention.

What is claimed is:

1. An implantable auditory stimulation system, comprising:
    a plurality of microphones, including at least a first microphone, operative to transcutaneously receive acoustic signals and generate a first microphone output signal in response thereto, and a second microphone operative to transcutaneously receive acoustic signals and generate a second output signal in response thereto;
    a processor, operatively interconnected to said first microphone and to said second microphone, adapted to use said first microphone output signal and said second microphone output signal to generate a drive signal; and,
    an implantable auditory stimulation device, operatively interconnected to said processor, adapted to stimulate an auditory system of a patient in response to said drive signal, wherein said first microphone has a first predetermined minimum sensitivity across a first predetermined frequency range, wherein said second microphone has a second predetermined minimum sensitivity across a second frequency range, and wherein said first and second predetermined frequency ranges are at least partially non-overlapping,
    wherein the first and second predetermined minimum sensitivities are sensitivities corresponding to a specified output signal having a given signal-to-noise ratio for an input having a given magnitude.

2. An implantable auditory stimulation system as recited in claim 1, further comprising:

a first implantable housing, wherein said first microphone is disposed within the implantable housing; and, a second implantable housing, wherein the second microphone is disposed within the second implantable housing, and wherein the first implantable housing and the second implantable housing are separately positionable.

3. An implantable auditory stimulation system as recited in claim 1, further comprising:

a flexible communication cable for use in operatively interconnecting at least one of said first microphone and said second microphone to said processor.

4. An implantable auditory stimulation system as recited in claim 3, wherein said flexible communication cable includes a connector end for selectively operative interconnection of the communications cable to and disconnect of the communication cable from said processor.

5. An implantable auditory stimulation system as recited in claim 2, wherein said processor is located in said first implantable housing.

6. An implantable auditory stimulation system as recited in claim 1, wherein said auditory stimulation device is one of a middle ear stimulation device and a neurostimulation device.

7. An implantable auditory stimulation system as recited in claim 1, wherein said processor comprises: a processing module for at least one of beamforming and directionality processing.

8. An implantable auditory stimulation system as recited in claim 1, further comprising:

a flexible communication cable having an end that is one of interconnected to, and interconnectable to and disconnectable from, said processor; and a connector that is one of interconnected to, and interconnectable to and disconnectable from, another end of said flexible communication cable, wherein said connector includes a first port, and wherein said second microphone is selectively interconnectable to and disconnectable from said first port of the connector.

9. An implantable auditory stimulation system as recited in claim 8, wherein said connector further includes a second port, and wherein said auditory stimulation device is selectively interconnectable to and disconnectable from said second port of the connector.

10. The implantable auditory stimulation system of claim 1, wherein the first and second predetermined minimum sensitivities are electrical device sensitivities.

11. An implantable auditory stimulation system, comprising:

a plurality of microphones, including at least a first microphone, operative to transcutaneously receive acoustic signals and generate a first microphone output signal in response thereto, and a second microphone operative to transcutaneously receive acoustic signals and generate a second output signal in response thereto;

a processor, operatively interconnected to said first microphone and to said second microphone, adapted to use said first microphone output signal and said second microphone output signal to generate a drive signal; and, an implantable auditory stimulation device, operatively interconnected to said processor, adapted to stimulate an auditory system of a patient in response to said drive signal, wherein said first microphone has a first predetermined minimum sensitivity across a first predetermined frequency range, wherein said second microphone has a second predetermined minimum sensitivity across a second frequency range, and wherein said first and second predetermined frequency ranges are at least partially non-overlapping, wherein said first microphone has a first predetermined minimum sensitivity of approximately −60 to −50 dBV/0.1 Pa across a first frequency range of 50 Hz to 3000 Hz, and wherein said second microphone has a second predetermined minimum sensitivity of approximately −60 to −50 dBV/0.1 Pa across a second predetermined frequency range of 1500 Hz to 10000 Hz.

12. The implantable auditory stimulation system of claim 11, wherein the first and second predetermined minimum sensitivities are sensitivities corresponding to a specified output signal having a given signal-to-noise ratio for an input having a given magnitude.

13. The implantable auditory stimulation system of claim 11, wherein the first and second predetermined minimum sensitivities are sensitivities expressible at least in part in terms of decibles and voltage.

14. An implantable auditory stimulation system as recited in claim 11, further comprising:

a first implantable housing, wherein said first microphone is disposed within the implantable housing; and, a second implantable housing, wherein the second microphone is disposed within the second implantable housing, and wherein the first implantable housing and the second implantable housing are separately positionable.

15. An implantable auditory stimulation system as recited in claim 11, further comprising:

a flexible communication cable for use in operatively interconnecting at least one of said first microphone and said second microphone to said processor.

16. An implantable auditory stimulation system as recited in claim 15, wherein said flexible communication cable includes a connector end for selectively operative interconnection of the communications cable to and disconnect of the communication cable from said processor.

17. An implantable auditory stimulation system as recited in claim 14, wherein said processor is located in said first implantable housing.

18. An implantable auditory stimulation system as recited in claim 11, wherein said auditory stimulation device is one of a middle ear stimulation device and a neurostimulation device.

19. An implantable auditory stimulation system as recited in claim 11, wherein said processor comprises: a processing module for at least one of beamforming and directionality processing.

20. An implantable auditory stimulation system as recited in claim 11, further comprising:

a flexible communication cable having an end that is one of interconnected to, and interconnectable to and disconnectable from, said processor; and a connector that is one of interconnected to, and interconnectable to and disconnectable from, another end of said flexible communication cable, wherein said connector includes a first port, and wherein said second microphone is selectively interconnectable to and disconnectable from said first port of the connector.

21. An implantable auditory stimulation system as recited in claim 20, wherein said connector further includes a second port, and wherein said auditory stimulation device is selectively interconnectable to and disconnectable from said second port of the connector.

22. An implantable auditory stimulation system, comprising:

a plurality of microphones, including at least a first microphone, operative to transcutaneously receive acoustic signals and generate a first microphone output signal in response thereto, and a second microphone operative to transcutaneously receive acoustic signals and generate a second output signal in response thereto;

a processor, operatively interconnected to said first microphone and to said second microphone, adapted to use said first microphone output signal and said second microphone output signal to generate a drive signal;

an implantable auditory stimulation device, operatively interconnected to said processor, adapted to stimulate an auditory system of a patient in response to said drive signal;

a flexible communication cable having an end that is one of interconnected to, and interconnectable to and disconnectable from, said processor; and a connector that is one of interconnected to, and interconnectable to and disconnectable from, another end of said flexible communication cable, wherein said connector includes a first port, and wherein said second microphone is selectively interconnectable to and disconnectable from said first port of the connector, wherein said first microphone has a first predetermined minimum sensitivity of approximately −60 to −50 dBV/0.1 Pa across a first frequency range of 50 Hz to 3000 Hz, and wherein said second microphone has a second predetermined minimum sensitivity of approximately −60 to −50 dBV/0.1 Pa across a second predetermined frequency range of 1500 Hz to 10000 Hz.

23. An implantable auditory stimulation system as recited in claim 22, wherein said first microphone has a first predetermined minimum sensitivity across a first predetermined frequency range, wherein said second microphone has a second predetermined minimum sensitivity across a second frequency range, and wherein said first and second predetermined frequency ranges are at least partially non-overlapping.

24. An implantable auditory stimulation system as recited in claim 22, wherein said connector further includes a second port, and wherein said auditory stimulation device is selectively interconnectable to and disconnectable from said second port of the connector.

25. An implantable auditory stimulation system as recited in claim 22, further comprising:
a first implantable housing, wherein said first microphone is disposed within the implantable housing; and,
a second implantable housing, wherein the second microphone is disposed within the second implantable housing, and wherein the first implantable housing and the second implantable housing are separately positionable.

26. An implantable auditory stimulation system as recited in claim 25, wherein said processor is located in said first implantable housing.

* * * * *